US007824852B2

(12) United States Patent
Olek et al.

(10) Patent No.: US 7,824,852 B2
(45) Date of Patent: *Nov. 2, 2010

(54) METHOD FOR DETECTING CYTOSINE METHYLATION IN DNA SAMPLES

(75) Inventors: Alexander Olek, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 532 days.

This patent is subject to a terminal disclaimer.

(21) Appl. No.: 10/220,896

(22) PCT Filed: Feb. 23, 2001

(86) PCT No.: PCT/DE01/00747

§ 371 (c)(1), (2), (4) Date: Mar. 11, 2003

(87) PCT Pub. No.: WO01/62960

PCT Pub. Date: Aug. 30, 2001

(65) Prior Publication Data

US 2003/0157510 A1 Aug. 21, 2003

(30) Foreign Application Priority Data

Feb. 25, 2000 (DE) ................. 100 10 282

(51) Int. Cl.
*C07H 21/04* (2006.01)
*C12Q 1/68* (2006.01)

(52) U.S. Cl. .......................... 435/6; 435/91.1; 435/91.2; 536/23.1; 536/24.3

(58) Field of Classification Search ........................ None
See application file for complete search history.

(56) References Cited

U.S. PATENT DOCUMENTS

| 5,391,480 | A | 2/1995 | Davis et al. | |
|---|---|---|---|---|
| 5,728,526 | A | 3/1998 | George, Jr. et al. | |
| 6,503,710 | B2 * | 1/2003 | Gut et al. ........................ | 435/6 |
| 2003/0129620 | A1 | 7/2003 | Olek et al. | |

FOREIGN PATENT DOCUMENTS

| WO | WO 95/00669 A | 1/1995 |
|---|---|---|
| WO | WO 98/44151 A | 10/1998 |
| WO | WO 98/56952 | * 12/1998 |
| WO | WO 99/28498 A | 6/1999 |
| WO | WO 99/55905 A | 11/1999 |

OTHER PUBLICATIONS

Newton et al. "Analysis of any point mutation in DNA. The amplification refractory mutation system (ARMS)", Nucleic Acids Research, vol. 17, No. 7, pp. 2503-2516, 1989.*
Gonzalgo et al. "Rapid quantitation of methylation differences at specific sites using methylation-sensitive single nucleotide primer extension (Ms-SNuPE)", Nucleic Acids Research, vol. 25, No. 12, pp. 2529-2531, 1997.*
Nyren et al. "Detection of single-base changes using a bioluminometric primer extension assay", Analytical Biochemistry, vol. 244, pp. 367-373, 1997.*
Nikiforov et al. "Genetic Bit Analysis: a solid phase method for typing single nucleotide polymorphisms", Nucleic Acids Research, vol. 22, No. 20, pp. 4167-4175, 1994.*
Pastinen et al. "Multiplex, fluorescent, solid-phase minisequencing for efficient screening of DNA sequence variation", Clinical Chemistry, vol. 42, No. 9, pp. 1391-1397, 1996.*
Bottema et al. (Mutation Research, vol. 288, pp. 93-102, 1993).*
Pastinen et al. (Genome Research, vol. 7, pp. 606-614, 1997).*
Radtke et al. Factor V R506Q genotype determination usina a single allele specific PCR reaction. Detection of PCR products on microtiter plates. Poster Session, Jun. 8, 1997.*
Gonzalgo et al., Nucleic Acids Research, 25(12):2529-31 (1997).
Grigg et al., "Sequencing 5-Methylcytosine Residues in Genomic DNA," Bioessays, 16(6):431-6 (1994).
Rein et al., "Identifying 5-methylcytosine and related modifications in DNA genomes," Nucleic Acids Research, 26(10):2255-64 (1998).
Paul et al., "Cytosine Methylation: Quantitation by Automated Genomic Sequencing and GENESCANtm Analysis," Biotechniques, 21:126-33 (1996).

(Continued)

*Primary Examiner*—Jeanine A Goldberg
(74) *Attorney, Agent, or Firm*—Kriegsman & Kriegsman

(57) ABSTRACT

Described is a method for detecting 5-methylcytosine in genomic DNA samples. First, a genomic DNA from a DNA sample is chemically converted with a reagent, 5-methylcytosine and cytosine reacting differently, and the pretreated DNA is subsequently amplified using a polymerase and at least one primer. In the next step, the amplified genomic DNA is hybridized to at least one oligonucleotide, forming a duplex, and said oligonucleotide is elongated by at least one nucleotide, the nucleotide carrying a detectable label, and the elongation depending on the methylation status of the specific cytosine in the genomic DNA sample. In the next step, the elongated oligonucleotides are analyzed for the presence of the label.

24 Claims, 1 Drawing Sheet

OTHER PUBLICATIONS

Niemeyer et al., "DNA Microarrays," Angew. Chem. Int. Ed., 38(19):3039-43 (1999).

Grunau et al., "Bisulfite genomic sequencing: systematic investigation of critical experimental parameters," Nucleic Acids Research, 29(13):e65 (pp. 1-7) (2001).

Gassen et al., "PCR Grundlage and Anwendungen der Polymerase-Kettenreaktion" 1994, Gustav Fischer Verlag, Stuttgart.

Communication of European Patent Office dated Sep. 23, 2005, in connection with European Patent Appln. No. 01 915 051.5-1222.

* cited by examiner

Spot 1  Spot 2

METHOD FOR DETECTING CYTOSINE METHYLATION IN DNA SAMPLES

BACKGROUND OF THE INVENTION

The present invention relates to a method for detecting 5-methylcytosine in genomic DNA samples.

The levels of observation that have been well studied by the methodological developments of recent years in molecular biology are the genes themselves, the translation of genes into RNA, and the resulting proteins. The question of which gene is switched on at which point in the course of the development of an individual, and how the activation and inhibition of specific genes in specific cells and tissues are controlled is correlatable to the degree and character of the methylation of the genes or of the genome.

The present invention describes a method for detecting the methylation state of genomic DNA samples. The method can, at the same time, also be used for detecting point mutations and single nucleotide polymorphisms (SNPs).

5-methylcytosine is the most frequent covalently modifiable base in the DNA of eukaryotic cells. It plays a role, for example, in the regulation of the transcription, in genetic imprinting, and in tumorigenesis. Therefore, the identification of 5-methylcytosine as a part of genetic information is of considerable interest. However, 5-methylcytosine positions cannot be identified by sequencing since 5-methylcytosine has the same base pairing behavior as cytosine. Moreover, the epigenetic information carried by the 5-methylcytosines is completely lost during a PCR amplification.

A relatively new and now the most frequently used method for analyzing DNA for 5-methylcytosine is based on the specific reaction of bisulfite with cytosine which, upon subsequent alkaline hydrolysis, is converted to uracil which corresponds to thymidine in its base pairing behavior. However, 5-methylcytosine remains unmodified under these conditions. Consequently, the original DNA is converted in such a manner that methylcytosine, which originally cannot be distinguished from cytosine in its hybridization behavior, can now be detected as the only remaining cytosine using "normal" molecular biological techniques, for example, by amplification and hybridization or sequencing. All these techniques are based on base pairing which is now taken full advantage of. The Prior Art is defined in terms of sensitivity by a method which encloses the DNA to be analyzed in an agarose matrix, thus preventing the diffusion and renaturation of the DNA (bisulfite reacts only on single-stranded DNA), and which replaces all precipitation and purification steps with fast dialysis (Olek, A. et al, Nucl. Acids. Res. 1996, 24, 5064-5066). Using this method, it is possible to analyze individual cells, which illustrates the potential of the method. Up to now, however, only individual regions of a length of up to approximately 3000 base pairs are analyzed; a global analysis of cells for thousands of possible methylation analyses is not possible. However, this method cannot reliably analyze very small fragments from small sample quantities either. These are lost in spite of the diffusion protection by the matrix.

An overview of the further known possibilities of detecting 5-methylcytosines can be gathered from the following survey article: Rein, T., DePamphilis, M. L., Zorbas, H., Nucleic Acids Res. 1998, 26, 2255.

Up to now, the bisulfite technology is only used in research with few exceptions (e.g., Zeschnigk M. et al, Eur J Hum Genet. 1997, 5, 94-98). Always, however, short specific fragments of a known gene are amplified subsequent to a bisulfite treatment and either completely sequenced (Olek, A. and Walter, J., Nat Genet. 1997, 17, 275-276) or individual cytosine positions are detected by a primer extension reaction (Gonzalgo, M. L., and Jones, P. A., Nucl. Acids Res. 1997, 25, 2529-2531, WO 9500669) or by an enzymatic digestion (Xiong, Z. and Laird, P. W., Nucl. Acids. Res. 1997, 25, 2532-2534). In addition, the detection by hybridization has also been described (Olek et al., WO 99 28498).

Further publications dealing with the use of the bisulfite technique for methylation detection in individual genes are: Xiong, Z. and Laird, P. W. (1997), Nucl. Acids Res. 25, 2532; Gonzalgo, M. L. and Jones, P. A. (1997), Nucl. Acids Res. 25, 2529; Grigg, S. and Clark, S. (1994), Bioassays 16, 431; Zeschnik, M. et al. (1997), Human Molecular Genetics 6, 387; Teil, R. et al. (1994), Nucl. Acids Res. 22, 695; Martin, V. et al. (1995), Gene 157, 261; WO 97 46705 and WO 95 15373.

An overview of the Prior Art in oligomer array manufacturing can be gathered from a special edition of Nature Genetics (Nature Genetics Supplement, Volume 21, January 1999), published in January 1999, and from the literature cited there.

There are different methods for immobilizing DNA. The best-known method is the fixed binding of a DNA which is functionalized with biotin to a streptavidin-coated surface (Uhlen, M. et al. 1988, Nucleic Acids Res. 16, 3025-3038). The binding strength of this system corresponds to that of a covalent chemical bond without being one. To be able to covalently bind a target DNA to a chemically prepared surface, a corresponding functionality of the target DNA is required. DNA itself does not possess any functionalization which is suitable. There are different variants of introducing a suitable functionalization into a target DNA: two functionalizations which are easy to handle are primary aliphatic amines and thiols. Such amines are quantitatively converted with N-hydroxysuccinimide esters, and thiols react quantitatively with alkyl iodides under suitable conditions. A difficulty consists in introducing such a functionalization into a DNA. The simplest variant is the introduction via a primer of a PCR. Disclosed variants use 5'-modified primers ($NH_2$ and SH) and a bifunctional linker.

An essential component of the immobilization on a surface is its constitution. Systems described up to now are mainly composed of silicon or metal. A further method of binding a target DNA is based on the use of a short recognition sequence (e.g., 20 bases) in the target DNA for hybridization to a surface-immobilized oligonucleotide. Enzymatic variants for introducing chemically activated positions in a target DNA have been described as well. In this case, a 5'-$NH_2$-functionalization is carried out enzymatically on a target DNA.

For scanning an immobilized DNA array, fluorescently labeled probes have often been used. Particularly suitable for fluorescence labeling is the simple attachment of Cy3 and Cy5 dyes to the 5'-OH of the specific probe. The detection of the fluorescence of the hybridized probes is carried out, for example via a confocal microscope. Cy3 and Cy5 dyes, besides many others, are commercially available.

More recent methods for detecting mutations are specified in the following:

Worth mentioning as a special case of sequencing is the single-base primer extension (Genetic Bit Analysis) (Head, S R., Rogers, Y H., Parikh K., Lan, G., Anderson, S., Goelet, P., Boycejacino M T., Nucleic Acids Research. 25(24): 5065-5071, 1997; Picoult-Newberg, L., Genome Res. 9(2): 167-174, 1999). A combined amplification and sequencing is described in U.S. Pat. No. 5,928,906 where a base-specific termination on matrix molecules is used. A further method uses a ligase/polymerase reaction for identifying nucleotides (U.S. Pat. No. 5,952,174).

Matrix Assisted Laser Desorption Ionization Mass Spectrometry (MALDI) is a very efficient development for the analysis of biomolecules (Karas, M. and Hillenkamp, F. (1988), Laser desorption ionization of proteins with molecular masses exceeding 10000 daltons. Anal. Chem. 60: 2299-2301). An analyte is embedded in a light-absorbing matrix. By a short laser pulse, the matrix is evaporated, thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones.

MALDI is ideally suited to the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157.). The sensitivity for nucleic acids is approximately 100 times worse than for peptides and decreases disproportionally with increasing fragment size. For nucleic acids having a multiply negatively charged backbone, the ionization process via the matrix is considerably less efficient. For MALDI, the selection of the matrix plays an eminently important role. For the desorption of peptides, several very efficient matrixes have been found which produce a very fine crystallization. For DNA, there are currently several matrixes in use, however, this has not reduced the difference in sensitivity. The difference in sensitivity can be reduced by chemically modifying the DNA in such a manner that it becomes more similar to a peptide. Phosphorothioate nucleic acids in which the usual phosphates of the backbone are substituted by thiophosphates can be converted into a charge-neutral DNA using simple alkylation chemistry (Gut, I. G. and Beck, S. (1995), A procedure for selective DNA alkylation and detection by mass spectrometry. Nucleic Acids Res. 23: 1367-1373). The coupling of a charge tag to this modified DNA results in an increase in sensitivity by the same amount as that found for peptides. A further advantage of charge tagging is the increased stability of the analysis against impurities which makes the detection of unmodified substrates considerably more difficult.

Genomic DNA is obtained from DNA of cell, tissue or other test samples using standard methods. This standard methodology is found in references such as Fritsch and Maniatis eds., Molecular Cloning: A Laboratory Manual, 1989.

Mutualities between promoters consist not only in the occurrence of TATA- or GC-boxes but also for which transcription factors they possess binding sites and at what distance these are located from each other. The existing binding sites for a specific protein do not match completely in their sequence but conserved sequences of at least 4 bases are found which can still be elongated by inserting wobbles, i.e., positions at which in each case different bases are located. Moreover, these binding sites are present at specific distances from each other. However, the distribution of the DNA in the interphase chromatin which occupies the largest portion of the nuclear volume is subject to a very special arrangement. Thus, the DNA is attached to the nuclear matrix, a filamentous pattern at the inner side of the nuclear membrane, at several locations. These regions are designated as matrix attachment regions (MAR) or scaffold attachment regions (SAR). The attachment has an essential influence on the transcription or the replication. These MAR fragments have no conserved sequences but to 70% they consist of A or T, and are located in the vicinity of cis-acting regions which regulate the transcription in a general manner, and in the vicinity of topoisomerase II recognition sites.

In addition to promoters and enhancers, further regulatory elements, so-called "insulators", exist for different genes. These insulators can, for example, inhibit the action of the enhancer on the promoter if they are located between enhancer and promoter, or else, if located between heterochromatin and a gene, can protect the active gene from the influence of the heterochromatin. Examples of such insulators include: firstly, so-called "LCR" (locus control regions) consisting of several sites which are hypersensitive to DNAase I; secondly, certain sequences such as SCS (specialized chromatin structures) or SCS', 350 or 200 bp long, respectively, and highly resistant to degradation by DNAase I, and flanked on both sides with hypersensitive sites (distance in each case 100 bp). The protein BEAF-32 binds to scs'. These insulators can be located on both sides of the gene.

SUMMARY OF THE INVENTION

It is the aim of the present invention to provide a method particularly suitable for concurrently detecting cytosine methylations and SNPs in genomic DNA samples. In the process, it should preferably be possible for a plurality of fragments to be analyzed concurrently.

The aim of the invention is reached by a method for detecting 5-methylcytosine in genomic DNA samples, wherein the following steps are carried out:

(a) a genomic DNA from a DNA sample is chemically converted with a reagent, 5-methylcytosine and cytosine reacting differently, thus exhibiting different base pairing behaviors in the DNA duplex subsequent to the reaction;

(b) pretreated DNA is amplified using a polymerase and at least one oligonucleotide (type A) as a primer;

(c) the amplified genomic DNA is hybridized to at least one oligonucleotide (type B) having a known sequence of n nucleotides, forming a duplex, said hybridized oligonucleotides of type B, with their 3'-ends, par-tially or completely hybridizing to the positions to be analyzed with regard to their methylation in the genomic DNA sample;

(d) the oligonucleotide (type B), provided that it has previously hybridized with its 3'-terminus to the position to be analyzed without mispairings, is elongated by at least one nucleotide by means of a polymerase, at least one nucleotide carrying a detectable label, and the elongation depending on the methylation status of the specific cytosine in the genomic DNA sample;

(e) the elongated oligonucleotides are analyzed for the presence of the label.

According to the invention it is preferred that the oligonucleotides (type B) are bonded to a solid phase at defined locations or that the amplificates are bonded to a solid phase at defined locations.

It is further preferred that different oligonucleotide sequences are arranged on a plane solid phase in the form of a rectangular or hexagonal lattice.

According to the invention it is further preferred that the solid phase surface is composed of silicon, glass, polystyrene, aluminum, steel, iron, copper, nickel, silver, or gold.

It is also preferred that the labels attached to the elongated oligonucleotides are identifiable at each position of the solid phase at which an oligonucleotide sequence is located.

According to the invention it is preferred that at least one primer (type A) is bonded to a solid phase during amplification.

Moreover it can be preferred according to the invention that different amplificates are arranged on the solid phase in the form of a rectangular or hexagonal lattice.

It is particularly preferred that, prior to the amplification, the DNA is treated with a bisulfite solution (=disulfite, hydrogen sulfite).

According to the invention it is particularly preferred that the amplification is carried out by means of the polymerase chain reaction (PCR).

According to the invention it is furthermore preferred that the oligonucleotides of type A either contain only the bases T, A and C or else the bases T, A und G.

It is further preferred that the labels of the nucleotides are fluorescence labels.

According to the invention it is further preferred that the labels of the nucleotides are radionuclides.

It is especially preferred that the labels of the nucleotides are detachable mass labels which are detected in a mass spectrometer.

According to the invention it is furthermore preferred that the elongated oligonucleotides altogether are detected in the mass spectrometer, thus being uniquely labeled by their masses. It is also particularly preferred that in each case one fragment of the elongated oligonucleotides is detected in the mass spectrometer.

According to the invention it is further preferred that the fragment of the elongated oligonucleotide is produced by digestion with one or several exo- or endonucleases.

According to the invention it is furthermore preferred that the produced fragments have a single positive or negative net charge for better detectability in the mass spectrometer.

According to the invention it is especially preferred that the detection of the elongated oligonucleotides is carried out and visualized by means of matrix assisted laser desorption/ionization mass spectrometry (MALDI) or using electron spray mass spectrometry (ESI).

According to the invention a method is preferred wherein the polymerases are heat-resistant DNA-polymerases.

According to the invention a method is also preferred wherein SNPs are also detected and visualized in addition to the DNA methylation.

Furthermore a method is preferred wherein the used nucleotides are terminating (type C 2) and/or chain-elongating nucleotides (type C 1).

According to the invention a method is further preferred wherein the nucleotides (type C 1 and C 2) are selected from a group comprising either the nucleobases A, T and C or else the bases G and A and T.

According to the invention it is further preferred that the amplification of several DNA segments is carried out in one reaction vessel.

Particularly preferred according to the invention is a method wherein the genomic DNA is obtained from a DNA sample, sources of DNA comprising, e.g., cell lines, blood, sputum, stool, urine, cerebral-spinal fluid, tissue embedded in paraffin, histologic object slides, and all possible combinations thereof.

Finally it is preferred according to the invention that the methylation analyses of the upper and lower DNA strand is carried out in one experiment.

BRIEF DESCRIPTION OF THE DRAWING

FIG. 1 shows that the amplified DNA hybridized on oligonucleotide SEQ-ID NO.:3 (spot 1) is only elongated during the primer extension reaction. Therefore, the analyzed CG position is not methylated.

DETAILED DESCRIPTION OF THE INVENTION

Figure 1:
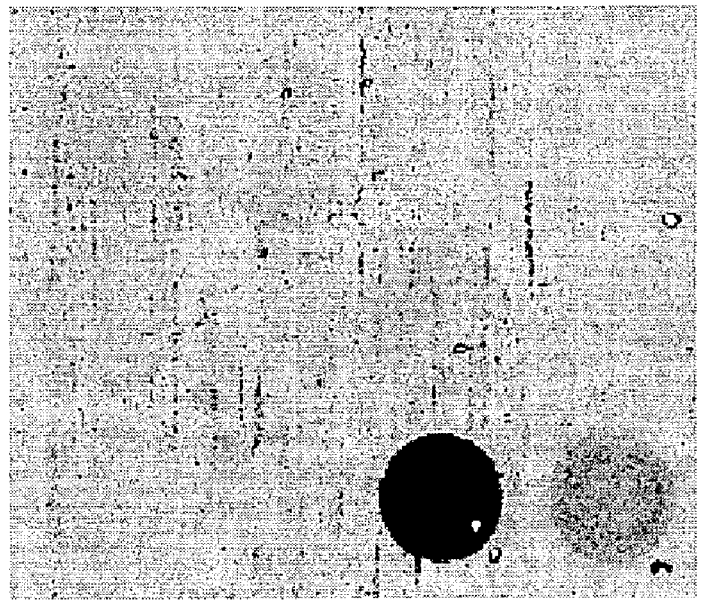
FIG. 1 illustrates the methylation analysis of a certain CG position of a fragment of exon 23 of the factor VIII gene (for details see example 3).

Described is a method for detecting methylcytosine in genomic DNA samples:

The method includes the amplification, hybridization and elongation reaction of an entire DNA or of a fragment thereof. The method can be used for detecting methylcytosine and, at the same time, also of single nucleotide polymorphisms (SNPs) and mutations.

The genomic DNA to be analyzed is preferably obtained from usual sources of DNA such as cell lines, blood, sputum, stool, urine, cerebral-spinal fluid, tissue embedded in paraffin, histologic object slides, and all possible combinations thereof.

In the first step of the method, the used DNA is preferably treated with bisulfite (=disulfite, hydrogen sulfite) or else with another chemical in such a manner that all cytosine bases which are not methylated at the 5-position of the base are changed in such a manner that a different base results with regard to the base pairing behavior while the cytosines methylated at the 5-position remain unchanged. If bisulfite is used, then an addition takes place at the non-methylated cytosine bases. The subsequent alkaline hydrolysis then gives rise to the conversion of non-methylated cytosine nucleobases to uracil.

In the second step of the method, the pretreated DNA is preferably amplified using a heat-resistant polymerase and at least one primer (type A).

In a particularly preferred variant of the method, the amplification is carried out with primers of type A by means of the polymerase chain reaction (PCR).

In a preferred variant of the method, the amplification of several DNA fragments is carried out in one reaction vessel. This can either be a so-called "multiplex PCR" in which different primers each produce defined fragments. Different, defined amplifications are carried out in one reaction vessel. In a further, particularly preferred variant of the method, primers in each case selectively and reproducibly amplify several fragments. This is achieved, for example, in that they bind, for example, to repetitive elements in the genome. In a particularly preferred variant of the method, the primers bind to transcription factor binding sites, to promoters or other regulatory elements in genes. In a particularly preferred variant of the method, the amplification is carried out by elongating primers which are bonded to a solid phase. A multiplex PCR in the broader sense can be carried out in that different primers are bonded at different, defined locations of a solid phase.

In an, again, preferred variant of the second method step, the solid phase is plane, the different oligonucleotide sequences being arranged in the form of a rectangular or hexagonal lattice. The result of this is that the different amplificates are arranged on the solid phase in the form of a rectangular or hexagonal lattice, as well. In this case, as already described above, several amplificates are directly produced on the solid phase.

The solid phase surface is preferably composed of silicon, glass, polystyrene, aluminum, steel, iron, copper, nickel, silver, or gold.

In a particularly preferred variant of the method, the oligonucleotides of type A either contain only bases T, A and C or only bases T, A und G.

In the third method step, the amplified genomic DNA is hybridized to at least one primer (type B), forming a duplex. The hybridized oligonucleotides of type B each bind at their 3'-end to the positions to be analyzed with regard to their methylation in the genomic DNA sample. In this context, two cases can be distinguished: the sequence to be analyzed is either completely complementary to the primer even at its 3'-end; in this case, it is possible to elongate the primer in a polymerase reaction in the next step, or else, the sequence is not completely complementary to that of the primer at the 3'-end; in this case, the primer cannot be elongated. If a specific CpG-position is to be analyzed for methylation, then there are two possible conditions. Subsequent to the chemical pretreatment, preferably with bisulfite, a CG occurs in the case of methylation; if an unmethylated cytosine is present, a UG or, subsequent to amplification, a TG ensue. In this case, the experiment is preferably carried out with two different primers which give rise to complete complementarity for one of the conditions, respectively, and, consequently, to the possibility of a chain elongation in one of the two possible cases, respectively.

Unless the amplificates are already bonded to the solid phase, then the oligonucleotides which are hybridized to the amplificates can be bonded to a solid phase with their 5'-end, or with another base, or via their backbone but not via their 3'-end. Preferably, the binding occurs via the 5'-end. In a preferred variant, the solid phase is plane, the different oligonucleotide sequences (type B) being arranged in the form of a rectangular or hexagonal lattice.

The solid phase surface is preferably composed of silicon, glass, polystyrene, aluminum, steel, iron, copper, nickel, silver, or gold.

In the fourth method step, the resulting oligonucleotide is elongated with a heat-resistant polymerase by at least one up to a maximum of ten nucleotides, at least one nucleotide carrying a detectable label. In this context, the type of elongation depends on the methylation status of the specific cytosine in the genomic DNA sample or else also on possibly existing SNPs, point mutations or deletions, insertions and inversions.

In principle, only terminating oligonucleotides (type C 2) are required. Depending on the sequence, however, chain-elongating oligonucleotides can be used as well provided that it is possible in the specific sequence context.

In a preferred variant of the method, the used nucleotides are terminating (type C 2) and/or chain-elongating nucleotides (type C 1). In a particularly preferred variant of the method, the nucleobases of type C1 and/or of type C 2 are selected from a group including bases T, A and C or else bases T, A and G.

The labeling of the elongated oligonucleotides of type B is preferably carried out via absorbing dyes and/or via chemiluminescence and/or via radioactive isotopes and/or via fluorescence labels which are introduced via the nucleotides added in the fourth method step. Also preferred is the labeling via the molecular mass of the elongated oligonucleotide. The fluorescence label is preferably inserted by a fluorescently labeled nucleotide such as Cy5-dCTP.

In the fifth method step, the elongated oligonucleotides are analyzed for the presence of a label. If a plane solid phase is used, then an analysis takes place at each location on the solid phase at which, originally, an oligonucleotide was immobilized.

In a particularly preferred variant of the method, the detection of the elongated oligonucleotides is carried out via their fluorescence.

In a preferred variant of the method, fragments of the elongated oligonucleotide are produced by digestion with one or several exo- or endonucleases.

In a particularly preferred variant of the method, the labels of the nucleotides are detachable mass labels which are detectable in a mass spectrometer.

In a particularly preferred variant of the method, detachable mass labels, the elongated oligonucleotides altogether or fragments thereof are detected and visualized on the basis of their unique mass by means of matrix assisted laser desorption/ionization mass spectrometry (MALDI-MS) or using electron spray mass spectrometry (ESI).

The fragments detected in the mass spectrometer preferably have a single positive or negative net charge.

In a particularly preferred variant of the method, SNPs (single nucleotide polymorphisms) and cytosine methylations are analyzed in one experiment.

In a particularly preferred variant of the method, the lower and the upper strand of the DNA sample is analyzed in one experiment subsequent to the chemical pretreatment to ensure an internal experimental control.

A further subject matter of the present invention is a kit containing chemicals and aids for carrying out the bisulfite reaction and/or the amplification, the hybridization, the elongation reaction and/or polymerases and/or the documentation for carrying out the method.

The following examples illustrate the invention.

Example 1

The following example relates to a fragment of exon 23 of the factor VIII gene in which a specific CG-position is to be analyzed for methylation.

In the first step, the fragment is amplified by primers of type A, namely by ATTATGTTGGAGTAGTAGAGTT-TAAATGGTT (SEQ.-ID No.: 1) and ACTTAACACTTAC-TATTTAAATCACAACCCAT (SEQ.-ID No.: 2). The amplified DNA is hybridized to an oligonucleotide of type B (for example, GTTGGATGTTGTTGAGAAACG (SEQ.-ID No.: 3)) and elongated in a polymerase reaction with a labeled 2',3'-didesoxythymidine triphosphat (type C 2). This elongation can only take place if a CG, that is, in the original genomic DNA sample, a methylated cytosine was present since otherwise, a mispairing at the 3'-end of the primer prevents the polymerase reaction. Thus, the methylation status of the specific cytosine to be analyzed decides on the elongation of the primer.

For control purposes, the reaction can be carried out with the primer GTTGGATGTTGTTGAGAAATG (SEQ.-ID No.: 4). In this case, the elongation takes place only if an non-methylated cytosine was present at said position in the DNA sample to be analyzed. The labels can, for example, be absorbing dyes such as Megaprime™ for ddTTP or Rediprime II™.

Example 2

The following example relates to a fragment of exon 23 of the factor VIII gene in which a specific CG-position is to be analyzed for methylation.

In the first step, the fragment is amplified by primers of type A, namely by ATTATGTTGGAGTAGTAGAGTT-TAAATGGTT (SEQ.-ID No.: 1) and ACTTAACACTTAC-TATTTAAATCACAACCCAT (SEQ.-ID No.: 2). The amplified DNA is hybridized to an oligonucleotide of type B (for example, GTTGGATGTTGTTGAGAAACG (SEQ.-ID No.: 3)), which is immobilized to a solid phase surface with its 5'-end, and elongated in a polymerase reaction with a labeled 2',3'-didesoxythymidine triphosphat (type C2). This elongation can only take place if a CG, that is, in the original genomic DNA sample, a methylated cytosine was present since otherwise, a mispairing at the 3'-end of the primer prevents the polymerase reaction. Thus, the methylation status of the specific cytosine to be analyzed decides on the elongation of the primer.

For control purposes, the reaction can be carried out with the primer GTTGGATGTTGTTGAGAAATG (SEQ.-ID No.: 4). In this case, the elongation takes place only if an non-methylated cytosine was present at said position in the DNA sample to be analyzed. The labels can, for example, be absorbing dyes such as Megaprime™ for ddTTP or Rediprime II™.

Example 3

The following example relates to a fragment of exon 23 of the factor VIII gene in which a specific CG-position is to be analyzed for methylation.

In the first step, the fragment is amplified by primers of type A, namely by ATTATGTTGGAGTAGTAGAGTT-TAAATGGTT (SEQ.-ID No.: 1) and ACTTAACACTTAC-TATTTAAATCACAACCCAT (SEQ.-ID No.: 2). For this amplification, DNA treated with bisulphite was incubated for 5 min at 96° C., then denaturated by 40 cycles carried out for 55 sec at 96° C. each, incubated for 75 sec at 61.7° C. (annealing) and incubated for 100 sec at 72° C. (elongation). In a subsequent reaction (final extension) the reaction mixture is incubated for 15 min at 72° C. The amplified DNA is hybridized to the solid phase immobilized oligonucleotides AAAAACTACAAAAACTCT (SEQ-ID No.: 5) (spot 1 in FIG. 1) and to AAAACTACGAAAACTCT (SEQ-ID No.: 6 (spot 2 in FIG. 1). The elongation reaction affords 2'-desoxythymidine triphosphate (dTTP, as type C 1), 2'-desoxyguanosine triphosphate (dGTP, as type C 1), 2'-desoxyadenosine triphosphat (dATP, as type C 1), and 2'-desoxycytidine triphosphate (dCTP, as type C 1), fluorescently labeled 2'-desoxycytidine triphosphate beeing added additionally in a 3:1 ratio (related to not-labeled 2'-desoxycytidine triphosphate). The reaction mixture, consisting of the amplificate, the desoxydinucleotide-mixture and 10× buffer is incubated for 15 min at 96° C. The Klenow fragment, used as a DNA polymerase herein, is added for the subsequent extension reaction and the reaction mixture is incubated at 37° C. on the solid phase overnight. As can be gathered from the following figure, the primer extension carried out suggest on the methylation status of the DNA. A comparison between spot 1 and spot 2, as illustrated in FIG. 1, allows a statement about the methylation status: in this case here the strength of the signal of spot 1 gives evidence to a non-methylated CpG.

The invention claimed is:

1. A method for detecting the methylation status of a cytosine position in genomic DNA samples, comprising:
   a) chemically treating a genomic DNA from a DNA sample with a reagent whereby 5-methylcytosine and cytosine react differently to said reagent, thus exhibiting different base pairing behaviors in the DNA duplex subsequent to the chemical treatment,
   b) amplifying the chemically treated DNA using a polymerase and at least one oligonucleotide (type A) as a primer,
   c) hybridizing the amplified genomic DNA to two oligonucleotides (type B) specific for DNA treated according to step (a) wherein
      (i) the 3'-ends of the oligonucleotides (type B) hybridize to the position to be analyzed with regard to its methylation in the genomic DNA sample
      (ii) the oligonucleotides (type B) are bonded to a solid support, and
      (iii) one oligonucleotide (type B) gives rise to complete complementarity in case of methylation while the other oligonucleotide gives rise to complete complementarity in case of non-methylation;
   d) elongating the one of the two oligonucleotides (type B) that has previously hybridized with its 3'-end to the position to be analyzed without mispairings by up to a maximum of ten nucleotides by means of a polymerase and a mixture of nucleotides
      wherein the elongation depends on the methylation status of the specific cytosine in the genomic DNA sample,
      wherein said mixture of nucleotides is either a mixture consisting of the nucleobases A, T, and C or a mixture consisting of the nucleobases G, A and T,
      wherein at least one of said nucleobases in said mixture is detectably labeled;
   e) comparing the signals derived from both oligonucleotides (type B) and deducing therefrom the methylation status of said cytosine position.

2. The method as recited in claim 1, characterized in that the amplificates are bonded to a solid phase at defined locations.

3. The method as recited in claim 1, characterized in that different oligonucleotide sequences are arranged on a plane solid phase in the form of a rectangular or hexagonal lattice.

4. The method as recited in claim 1, characterized in that solid phase surface is composed of silicon, glass, polystyrene, aluminum, steel, iron, copper, nickel, silver, or gold.

5. The method as recited in claim 1, characterized in that the labels attached to the elongated oligonucleotides are identifiable at each position of the solid phase at which an oligonucleotide sequence is located.

6. The method as recited in claim 1, characterized in that at least one primer (type A) is bonded to a solid phase during amplification.

7. The method as recited in claim 1, characterized in that different amplificates are arranged on the solid phase in the form of a rectangular or hexagonal lattice.

8. The method as recited in claim 1, characterized in that, prior to the amplification, the DNA is treated with a bisulfite solution (=disulfite, hydrogen sulfite).

9. The method as recited in claim 1, characterized in that the amplification is carried out by means of the polymerase chain reaction (PCR).

10. The method as recited in claim 1, characterized in that the oligonucleotides of type A used in claim 1 either contain only the bases T, A and C or else the bases T, A and G.

11. The method as recited in claim 1, characterized in that the labels of the nucleotides are fluorescence labels.

12. The method as recited in claim 1, characterized in that the labels of the nucleotides are radionuclides.

13. The method as recited in claim 1, characterized in that the labels of the nucleotides are detachable mass labels which are detected in a mass spectrometer.

14. The method as recited in claim 1, characterized in that the elongated oligonucleotides altogether are detected in the mass spectrometer, thus being uniquely labeled by their masses.

15. The method as recited in claim 1, characterized in that in each case one fragment of the elongated oligonucleotides is detected in the mass spectrometer.

16. The method as recited in claim 15, characterized in that the fragment of the elongated oligonucleotide is produced by digestion with one or several exo- or endonucleases.

17. The method as recited in claim 16, characterized in that the produced fragments have a single positive or negative net charge for better detectability in the mass spectrometer.

18. The method as recited in claim 1, characterized in that the detection of the elongated oligonucleotides is carried out and visualized by means of matrix assisted laser desorption/ionization mass spectrometry (MALDI) or using electron spray mass spectrometry (ESI).

19. The method as recited in claim 1, wherein the polymerases are heat-resistant DNA-polymerases.

20. The method as recited in claim 1, wherein SNPs are also detected and visualized in addition to the DNA methylation.

21. The method as recited in claim 1, wherein the nucleotides used for elongation comprise at least one of terminating nucleotides and chain-elongating nucleotides.

22. The method as recited in claim 1, characterized in that the amplification of several DNA segments is carried out in one reaction vessel.

23. The method as recited in claim 1, step a, wherein the genomic DNA is obtained from a DNA sample, sources of DNA comprising cell lines, blood, sputum, stool, urine, cerebral-spinal fluid, tissue embedded in paraffin, histologic object slides, and all possible combinations thereof.

24. The method as recited in claim 1, characterized in that the methylation analyses of the upper and lower DNA strands are carried out in one experiment.

* * * * *

SEQUENCE LISTING

<160> NUMBER OF SEQ ID NOS: 6

<210> SEQ ID NO 1
<211> LENGTH: 31
<212> TYPE: DNA
<213> ORGANISM: artificial sequence
<220> FEATURE:
<223> OTHER INFORMATION: oligonucleotide

<400> SEQUENCE: 1
attatgttgg agtagtagag tttaaatggt t                               31

<210> SEQ ID NO 2
<211> LENGTH: 32
<212> TYPE: DNA
<213> ORGANISM: artificial sequence
<220> FEATURE:
<223> OTHER INFORMATION: oligonucleotide

<400> SEQUENCE: 2
acttaacact tactatttaa atcacaaccc at                              32

<210> SEQ ID NO 3
<211> LENGTH: 21
<212> TYPE: DNA
<213> ORGANISM: artificial sequence
<220> FEATURE:
<223> OTHER INFORMATION: oligonucleotide

<400> SEQUENCE: 3
gttggatgtt gttgagaaac g                                          21

-continued

```
<210> SEQ ID NO 4
<211> LENGTH: 21
<212> TYPE: DNA
<213> ORGANISM: artificial sequence
<220> FEATURE:
<223> OTHER INFORMATION: oligonucleotide

<400> SEQUENCE: 4
gttggatgtt gttgagaaat g                                         21

<210> SEQ ID NO 5
<211> LENGTH: 18
<212> TYPE: DNA
<213> ORGANISM: artificial sequence
<220> FEATURE:
<223> OTHER INFORMATION: oligonucleotide

<400> SEQUENCE: 5
aaaaactaca aaaactct                                             18

<210> SEQ ID NO 6
<211> LENGTH: 18
<212> TYPE: DNA
<213> ORGANISM: artificial sequence
<220> FEATURE:
<223> OTHER INFORMATION: oligonucleotide

<400> SEQUENCE: 6
aaaaactacg aaaactct                                             18
```